United States Patent
Zhang

(10) Patent No.: US 7,316,713 B2
(45) Date of Patent: Jan. 8, 2008

(54) ACCOMMODATIVE INTRAOCULAR LENS SYSTEM

(75) Inventor: Xiaoxiao Zhang, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 189 days.

(21) Appl. No.: 11/214,318

(22) Filed: Aug. 29, 2005

(65) Prior Publication Data

US 2007/0050024 A1    Mar. 1, 2007

(51) Int. Cl.
*A61F 2/16* (2006.01)

(52) U.S. Cl. .................. 623/6.37; 623/6.34; 623/6.4

(58) Field of Classification Search ............ 623/6.34, 623/6.37, 6.39, 6.4, 6.43
See application file for complete search history.

(56) References Cited

U.S. PATENT DOCUMENTS

| | | | |
|---|---|---|---|
| 5,275,623 A | 1/1994 | Sarfarazi | |
| 5,476,514 A | 12/1995 | Cumming | |
| 5,496,366 A | 3/1996 | Cumming | |
| 5,674,282 A | 10/1997 | Cumming | |
| 6,197,059 B1 | 3/2001 | Cumming | |
| 6,241,777 B1 | 6/2001 | Kellan | |
| 6,261,321 B1 | 7/2001 | Kellan | |
| 6,302,911 B1 | 10/2001 | Hanna | |
| 6,616,691 B1 * | 9/2003 | Tran | 623/6.11 |
| 6,695,881 B2 * | 2/2004 | Peng et al. | 623/6.34 |
| 6,926,736 B2 * | 8/2005 | Peng et al. | 623/6.34 |
| 2002/0107568 A1 | 8/2002 | Zadno-Azizi et al. | |
| 2004/0039446 A1 | 2/2004 | McNicholas | |

FOREIGN PATENT DOCUMENTS

| | | |
|---|---|---|
| WO | WO 01/34067 | 11/1999 |
| WO | WO 00/66037 | 11/2000 |
| WO | WO 03/059196 | 7/2003 |
| WO | WO 03/059208 | 7/2003 |

OTHER PUBLICATIONS

"A dual optic accommodating foldable intraocular lens" *British Journal of Ophthalmology* 2003;87:1083-1085.

* cited by examiner

*Primary Examiner*—William H Matthews
(74) *Attorney, Agent, or Firm*—Jeffrey S. Schira

(57) ABSTRACT

A two optic accommodative lens system. The present invention also contemplates the use of a cam mechanism to adjust the distance power via adjustment of the dual lens separation when the eye is at distance vision stasis. The cam mechanism allows for distance/base power adjustment as needed.

7 Claims, 5 Drawing Sheets

ACCOMMODATIVE INTRAOCULAR LENS SYSTEM

BACKGROUND OF THE INVENTION

This invention relates generally to the field of intraocular lenses (IOL) and, more particularly, to accommodative IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In the way, the natural lens can be focus alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Prior to the present invention, when a cataract or other disease required the removal of the natural lens and replacement with an artificial IOL, the IOL was a monofocal lens, requiring that the patient use a pair of spectacles or contact lenses for near vision. Advanced Medical Optics has been selling a bifocal IOL, the Array lens, for several years, but due to quality of issues, this lens has not been widely accepted.

Several designs for accommodative IOLs are being studied. For example, several designs manufactured by C&C Vision are currently undergoing clinical trials. See U.S. Pat. Nos. 6,197,059, 5,674,282, 5,496,366 and 5,476,514 (Cumming), the entire contents of which being incorporated herein by reference. The lens described in these patents is a single optic lens having flexible haptics that allows the optic to move forward and backward in reaction to movement of the ciliary muscle. A similar designs are described in U.S. Pat. No. 6,302,911 B1 (Hanna), U.S. Pat. Nos. 6,261,321 B1 and 6,241,777 B1 (both to Kellan), the entire contents of which being incorporated herein by reference. The amount of movement of the optic in these single-lens systems, however, may be insufficient to allow for a useful range of accommodation. In addition, as described in U.S. Pat. Nos. 6,197,059, 5,674,282, 5,496,366 and 5,476,514, the eye must be paralyzed for one to two weeks in order for capsular fibrosis to entrap the lens that thereby provide for a rigid association between the lens and the capsular bag. In addition, the commercial models of these lenses are made from a hydrogel or silicone material. Such materials are not inherently resistive to the formation of posterior capsule opacification ("PCO"). The only treatment for PCO is a capsulotomy using a Nd:YAG laser that vaporizes a portion of the posterior capsule. Such destruction of the posterior capsule may destroy the mechanism of accommodation of these lenses.

There have been some attempts to make a two-optic accommodative lens system. For example, U.S. Pat. No. 5,275,623 (Sarfarazi), WIPO Publication No. 00/66037 (Glick, et al.) and WO 01/34067 A1 (Bandhauer, et al), the entire contents of which being incorporated herein by reference, all disclose a two-optic lens system with one optic having a positive power and the other optic having a negative power. The optics are connected by a hinge mechanism that reacts to movement of the ciliary muscle to move the optics closer together or further apart, thereby providing accommodation. In order to provide this "zoom lens" effect, movement of the ciliary muscle must be adequately transmitted to the lens system through the capsular bag, and none of these references disclose a mechanism for ensuring that there is a tight connection between the capsular bag and the lens system. In addition, none of these lenses designs have addressed the problem with PCO noted above.

Prior art accommodative two lens systems using a movable "zoom" lens have inherently limited movement. The maximum sensitivity or movement magnification a (a unitless ratio) is defined as the axial movement of the lens per unit zonule movement and is derived by the following equation:

$$\alpha = -B/A$$

where B is the projected distance of the zonule length which is in the order of 1.0 to 2.0 mm; and A is the axial distance between the middle plane between the dual lens and the anterior surface of the anterior lens where the zonules terminate.

Practically speaking, because of the lens thickness and dual lens separation requirement, A cannot be less than ~1 mm. Therefore, $\alpha$ cannot be larger than 2, which defines the limit of the known dual lens accommodative approaches. This limit is too low for the dual optics design to achieve the objective of creating the greater than 2.25 diopters of accommodative amplitude that patients need for normal accommodation, which ideally results in a greater than or equal to 4.

Secondly, existing dual optics accommodative implants do not manage any necessary change in the base power of the dual optics lens systems. Such changes can result from the inaccuracy of biometry, surgical variations, implant variations and inter-patient capsule variations. Consequently, patients can have refractive error after the implantation and need additional spectacles corrections that are not desired. In addition, potential post implantation capsule reaction and other ocular changes over time can result in the gradual development of refractive errors over time.

Therefore, a need continues to exist for a safe and stable accommodative intraocular lens that provides accommodation over a broad and useful range and an adjustable base power.

BRIEF SUMMARY OF THE INVENTION

The present invention improves upon the prior art by providing a two optic accommodative lens system. The present invention also contemplates the use of a cam mechanism to adjust the distance power via adjustment of the dual lens separation when the eye is at distance vision stasis. The cam mechanism allows for distance/base power adjustment as needed.

Accordingly, one objective of the present invention is to provide a safe and biocompatible intraocular lens system.

Another objective of the present invention is to provide a safe and biocompatible intraocular lens system that is easily implanted in the posterior chamber.

Still another objective of the present invention is to provide a safe and biocompatible intraocular lens system that is stable in the posterior chamber.

Still another objective of the present invention is to provide a safe and biocompatible accommodative lens system.

Still another objective of the present invention is to provide a safe and biocompatible accommodative lens system having an adjustable base power.

These and other advantages and objectives of the present invention will become apparent from the detailed description and claims that follow.

DETAILED DESCRIPTION OF THE INVENTION

Figure 1A:
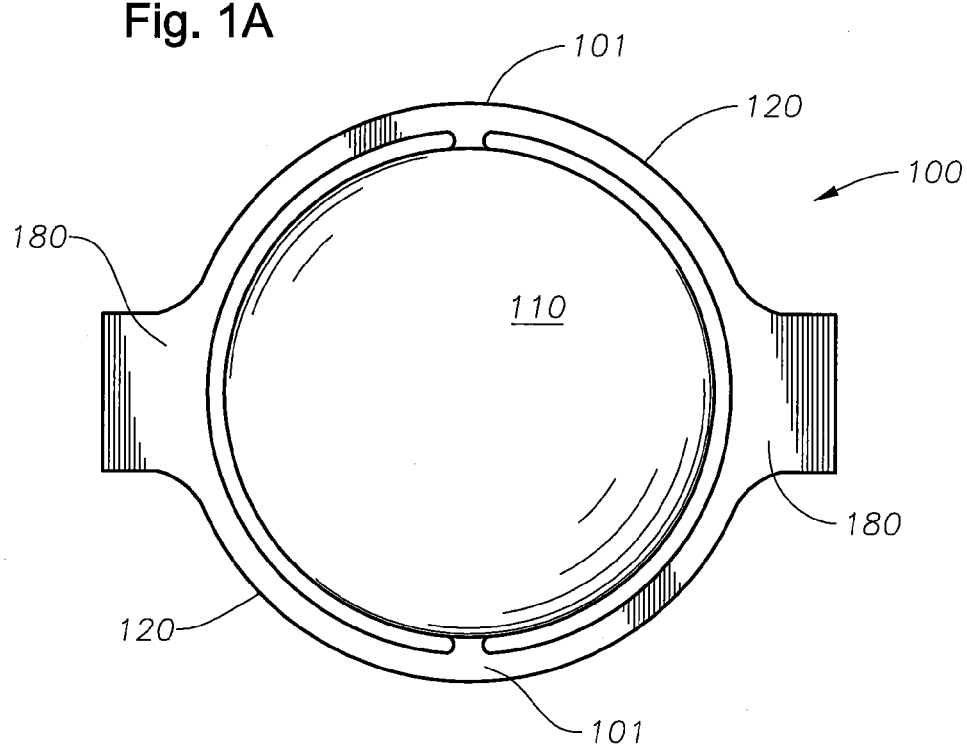
FIG. 1A is an enlarged top plan view of the first lens of the lens system of the present invention.
Figure 1B:
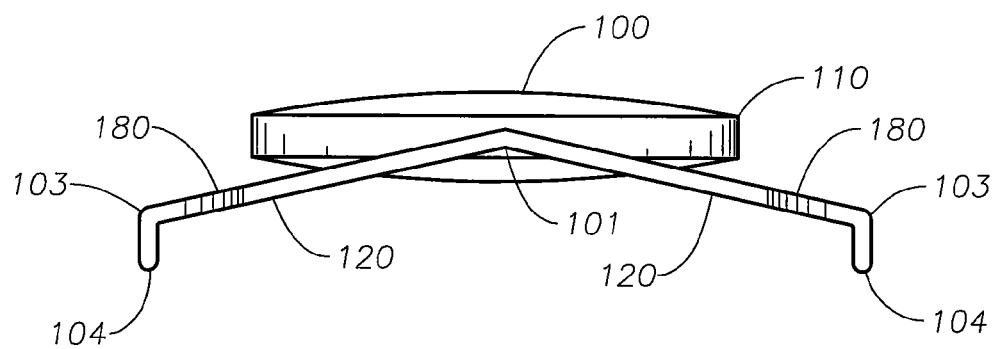
FIG. 1B is an enlarged elevational view of the first lens of the lens system of the present invention.
Figure 2A:
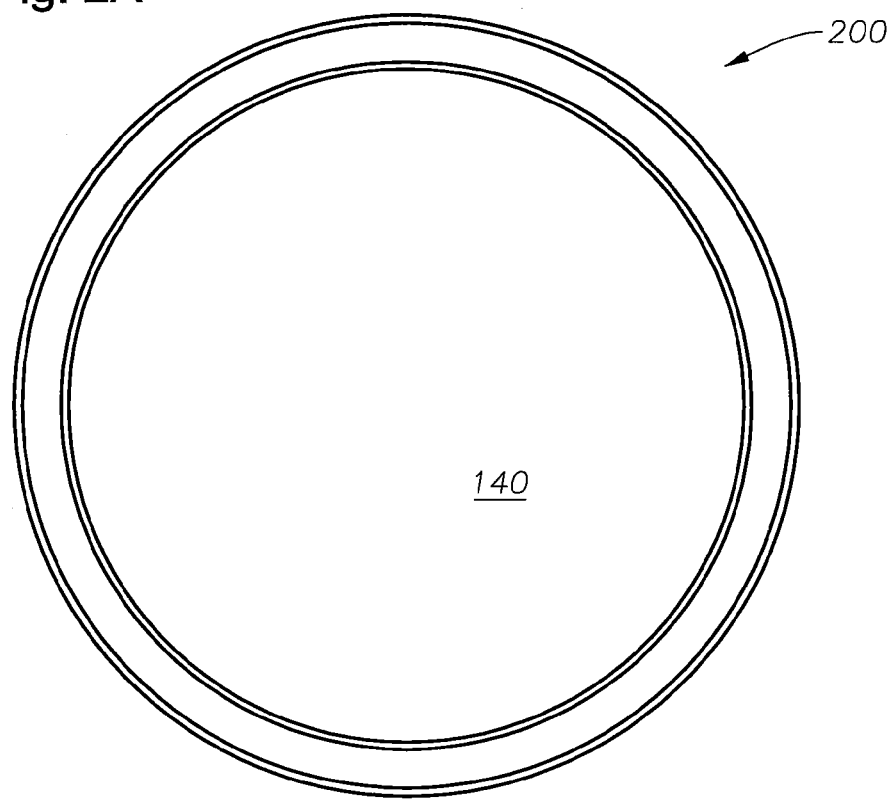
FIG. 2A is an enlarged top plan view of the force transfer ring of the lens system of the present invention.
Figure 2B:
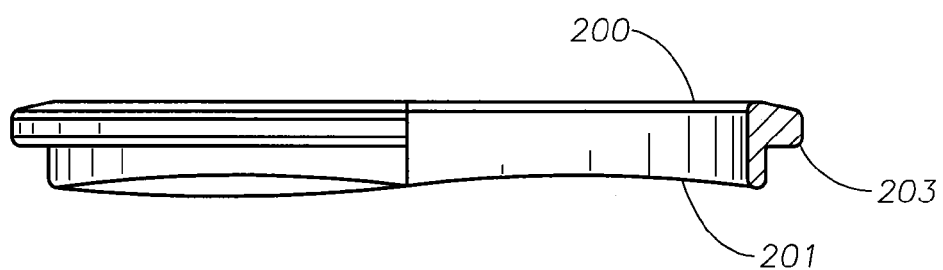
FIG. 2B is an enlarged partial cross-sectional view of the force transfer ring of the lens system of the present invention.
Figure 3A:
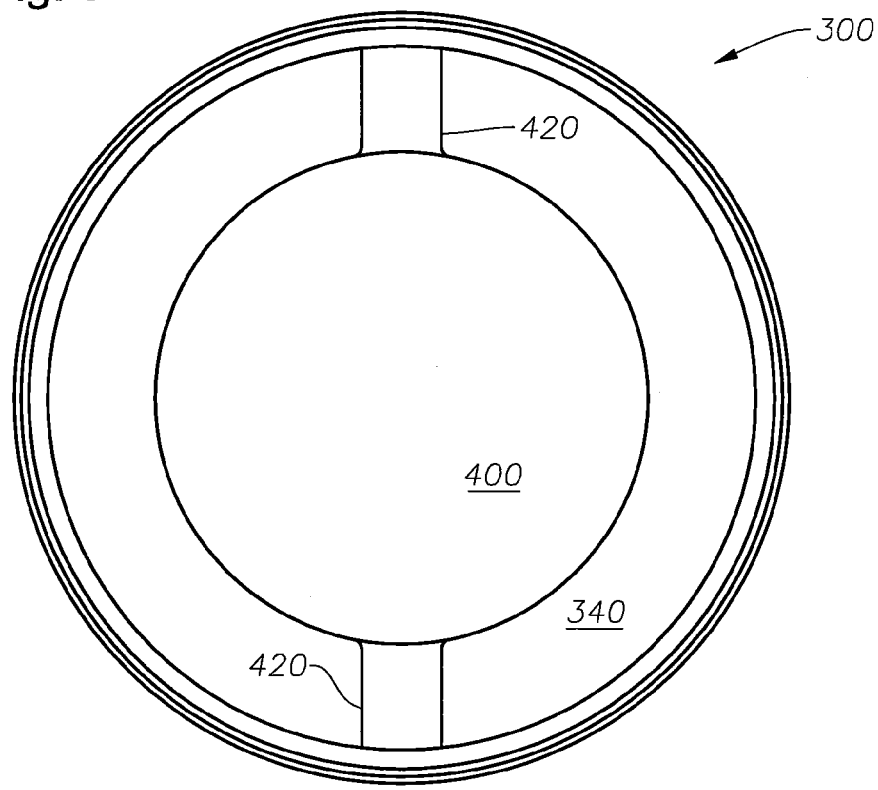
FIG. 3A is an enlarged top plan view of the capsule ring and second lens of the lens system of the present invention.
Figure 3B:
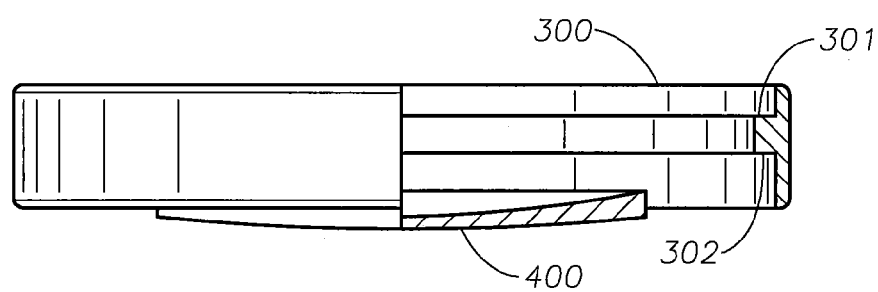
FIG. 3B is an enlarged partial cross-sectional view of the capsule ring and second lens of the lens system of the present invention.

As best seen in FIGS. 1A–1B, first, or anterior lens 100 of the present invention generally includes first optic 110 and attached haptics 120. Haptics 120 are attached to optic 110 by hinges 101. Haptics 120 generally encircle optic 110 and contain widened tabs 180 having downward turn edges 104. Tabs 180 are formed in a vaulted position, as best seen in FIG. 1B so that edge 104 lays in a plane separated from the plane in which optic 110 lays. As best seen in FIGS. 2A–2B, force transfer ring 200 is generally circular having a central bore 140 into which anterior lens 100 fits. Ring 200 contains camming surface 201 that rests on tabs 180 on haptics 120 in the manner described below. Ring 200 further contains outer circumferential rim 203. As best seen in FIGS. 3A–3B, outer ring 300 is generally circular having a central bore 340 into which ring 200 fits. Ring 300 further contains internal circumferential ledge 301 on which rim 204 rests when ring 200 is fitted within ring 300. Attached to ring 300 by haptics 420 is second or posterior lens 400. Lenses 100 and 400 may be made from any suitable material such as a thermoplastic, a silicone, a hydrogel or a soft acrylic and contain any desired additives, such as ultraviolet or blue light blocking chromophores. Lenses 100 and 400 may further have any suitable design, such aspheric, toric, pseudoaccommodative or multifocal. Those skilled in the art will recognize that lenses 100 and 400 need not be implanted at the same time. For example, lens 400 and ring 300 may be implanted in an eye and the eye allowed to recover from the surgical trauma. After waiting such a healing period, bioptric and other physiological measurements may be made sufficient to calculate an accurate prescription for lens 100, at which time lens 100 and ring 200 may be implanted.

Figure 4A:
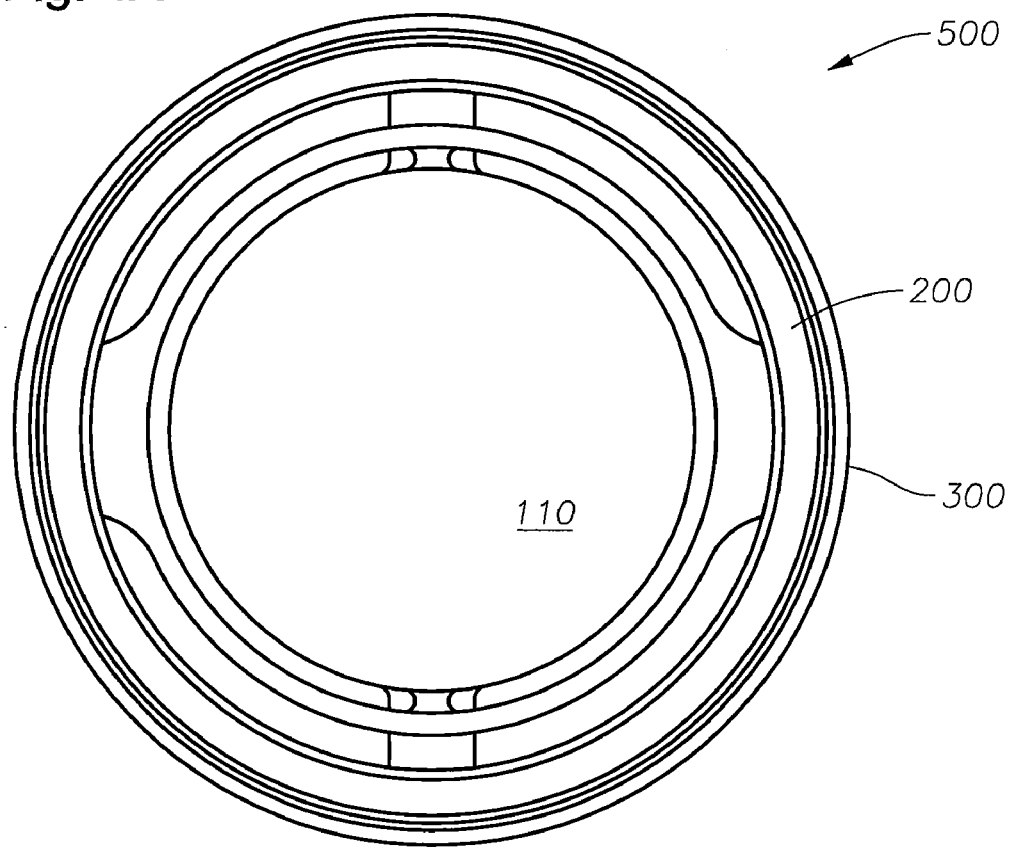
FIG. 4A is an enlarged plan view of the lens system of the present invention shown in its low power, or distance vision state.
Figure 4B:
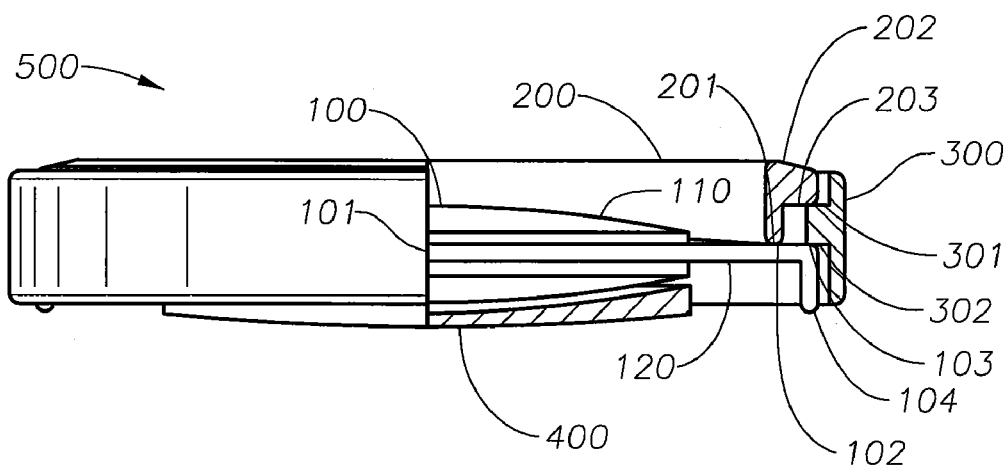
FIG. 4B is an enlarged partial cross-sectional view of the lens system of the present invention shown in its low power, or distance vision state.
Figure 5:
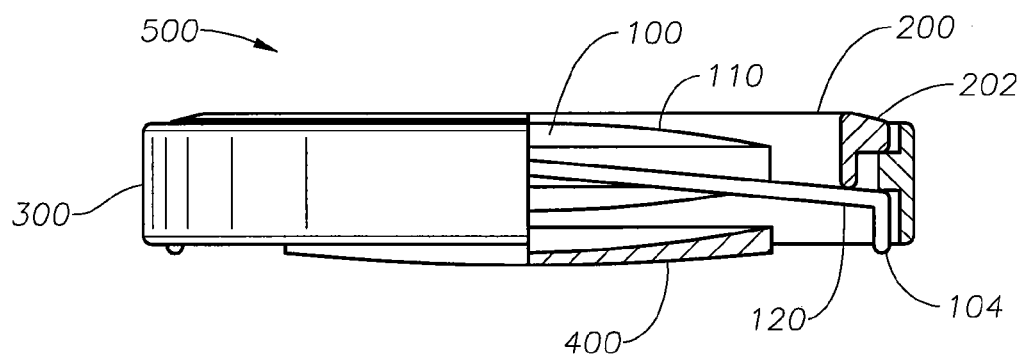
FIG. 5 is an enlarged partial cross-sectional view of the lens system of the present invention in its medium power, or intermediate vision position.
Figure 6:
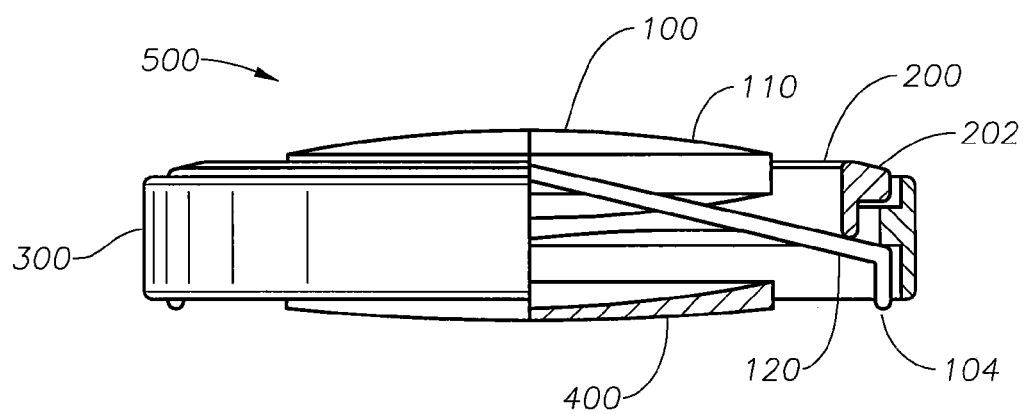
FIG. 6 is an enlarged partial cross-sectional view of the lens system of the present invention in its high power, or near vision state.

As best seen in FIGS. 4–6, lens assembly 500 is assembled within in an eye by first implanting outer ring 300 containing posterior lens 400 within the capsular bag. Anterior lens 100 is then placed within ring 300 in front of posterior lens 400 so that widened tabs 180 are caught under lower rim 302 of circumferential ledge 301 on ring 300. Ring 200 is then placed within ring 300 so that camming surface 210 rests on tabs 180 of haptics 120 and circumferential rim 203 rests on circumferential ledge 301. As show in FIGS. 4A–4B, lens assembly 500 is at its low power state—distance vision state. This state is achieved via the following sequence. When there is a need to dis-accommodate—to see distance objects, the ciliary muscle relaxes to cause enlargement of the ciliary ring diameter. The enlargement of the ciliary ring pulls the zonules outward in radial directions. Such outward zonule movement causes the anterior and posterior capsule portions to move towards each other. In other words, the capsular bag flattens. Flattening of the capsular bag causes ring 200 and edge 104 on haptic 120 of lens 100 to move toward each other because the anterior capsule portion (not shown) contacts ring 200 at anterior edge 202, and because the posterior capsule portion (not shown) contacts lens 100 at edge 104 of haptic 120. The movement stops when circumferential rim 203 rests on circumferential ledge 301 and when distal end 103 of tab 180 meets lower rim 302. In this position, camming rim 201 presses against tabs 180 at area 102. Consequently, hinge 101 is in a flexed, tensioned or sprung position. In this dis-accommodative position, the separation between anterior lens 100 and posterior lens 400 together with the respective powers of the two lenses determines the actual power of the lens assembly 500.

FIGS. 5–6, show lens assembly 500 in accommodative positions. As one needs to accommodate—to see near objects, the ciliary muscle contracts causing ciliary ring diameter reduction. This reduction relaxes the holding force of the zonules, no longer flattening the capsule bag. With the capsular bag no longer holding haptics 120 and optic 110 flat, the tension in hinges 101 cause edges 104 to move away from optic 110, thereby returning lens 110 into its natural vaulted state. Such vaulting moves lens 100 away from lens 400, thereby causing an increase in lens separations resulting in an overall higher power of dual lens assembly 500. The leverage ratio is determined by the ratio of the length of haptic 120 from hinge 101 to area 102, and the length from area 102 to distal end 103. By design adjustment, a higher ratio can be achieved such that the axial movement of optic 110 is much larger than that of ring 200. Therefore, the amount of axial movement of optic 110 is not limited to the amount of axial movement of the anterior capsule, so that $\alpha > 2.25$ can be achieved.

In order to provide power adjustability to lens assembly 500, as best seen in FIG. 2B, camming surface 201 on ring 200 is not straight, but has an undulating profile, so that the distance between camming surface 201 and anterior edge 202 varies. Rotation of ring 200 causes variable axial movement of optic 110 because camming rim 201 presses against tabs 180 at area 102, such pressure causing flexure of hinges 101.

This description is given for purposes of illustration and explanation. It will be apparent to those skilled in the relevant art that changes and modifications may be made to the invention described above without departing from its scope or spirit.

I claim:

1. An intraocular lens system, comprising:
   a) a first lens having an optic and a first pair of encircling haptics, the haptics having opposing widened tabs with downwardly turned edges, the haptics being attached to the optic by a pair of hinges;
   b) a second lens attached to an outer ring by a second set of haptics, the outer ring containing an internal circumferential ledge and being sized to telescopically receive the first lens; and
   c) a force transfer ring having an outer circumferential rim telescopically received within the outer ring anteriorly of the first lens.

2. The lens system of claim 1 wherein the force transfer ring further comprises a camming surface.

3. The lens system of claim 2 wherein the camming surface contacts the widened tabs of the first lens.

4. The lens system of claim 3 wherein the hinges allow the first lens to move anteriorly and posteriorly when implanted in an eye and rotation of the force transfer ring variably limits the movement of the first lens.

5. An intraocular lens system, comprising:
   a) a first lens having an optic and a first pair of encircling haptics, the haptics having opposing widened tabs with downwardly turned edges, the haptics being attached to the optic by a pair of hinges;
   b) a second lens attached to an outer ring by a second set of haptics, the outer ring containing an internal circumferential ledge, the outer ring being sized to telescopically receive the first lens so that the circumferential ledge retains the first lens within the outer ring anteriorly of the second lens; and
   c) a force transfer ring having an outer circumferential rim and a camming surface that contacts the widened tabs of the first lens, the force transfer ring being telescopically received within the outer ring anteriorly of the first lens.

6. The lens system of claim 5 wherein the camming surface contacts the widened tabs of the first lens.

7. The lens system of claim 6 wherein the hinges allow the first lens to move anteriorly and posteriorly when implanted in an eye and rotation of the force transfer ring variably limits the movement of the first lens.

\* \* \* \* \*